United States Patent [19]

Oretorp

[11] 4,444,184

[45] Apr. 24, 1984

[54] SURGICAL INSTRUMENT FOR OPERATING ON JOINTS

[75] Inventor: Nils Oretorp, Linköping, Sweden

[73] Assignee: Aktiebolaget Stille-Werner, Stockholm, Sweden

[21] Appl. No.: 962,262

[22] Filed: Nov. 20, 1978

[30] Foreign Application Priority Data

Nov. 29, 1977 [SE] Sweden .............................. 7713526

[51] Int. Cl.³ ............................................ A61B 17/32
[52] U.S. Cl. ................................................... 128/305
[58] Field of Search .................. 128/305, 314, 329 R, 128/751, 757, 759; 30/162

[56] References Cited

U.S. PATENT DOCUMENTS

| | | | |
|---|---|---|---|
| 3,762,416 | 10/1973 | Moss et al. | 128/305 |
| 3,902,498 | 9/1975 | Niederer | 128/305 |
| 3,945,375 | 3/1976 | Banko | 128/305 X |
| 3,994,297 | 11/1976 | Kopf | 128/305 X |
| 4,089,112 | 5/1978 | Richards | 30/162 |

FOREIGN PATENT DOCUMENTS

| | | | |
|---|---|---|---|
| 1102799 | 10/1955 | France | 128/329 |
| 1235321 | 6/1971 | United Kingdom | 128/303 R |

*Primary Examiner*—Michael H. Thaler

[57] ABSTRACT

A surgical instrument is provided for performing operations on joints, comprising an elongated hollow body; an elongated tube fixedly connected at one end to the body and adapted for insertion into a joint at a selected location; a manipulator shaft axially movable in the tube and in the body; a substantially planar cutting member on one end of the shaft; and member manipulatable by the fingers to move the shaft between a first position in which the cutting member is withdrawn within the tube and a second position in which the cutting member is extended beyond the end of the tube; the tube having a rounded closed end with a slot therethrough through which the cutting member is extended and withdrawn and effective to guide the cutting member during such movement and to restrain the cutting member against rotation during such movement and while cutting.

12 Claims, 3 Drawing Figures

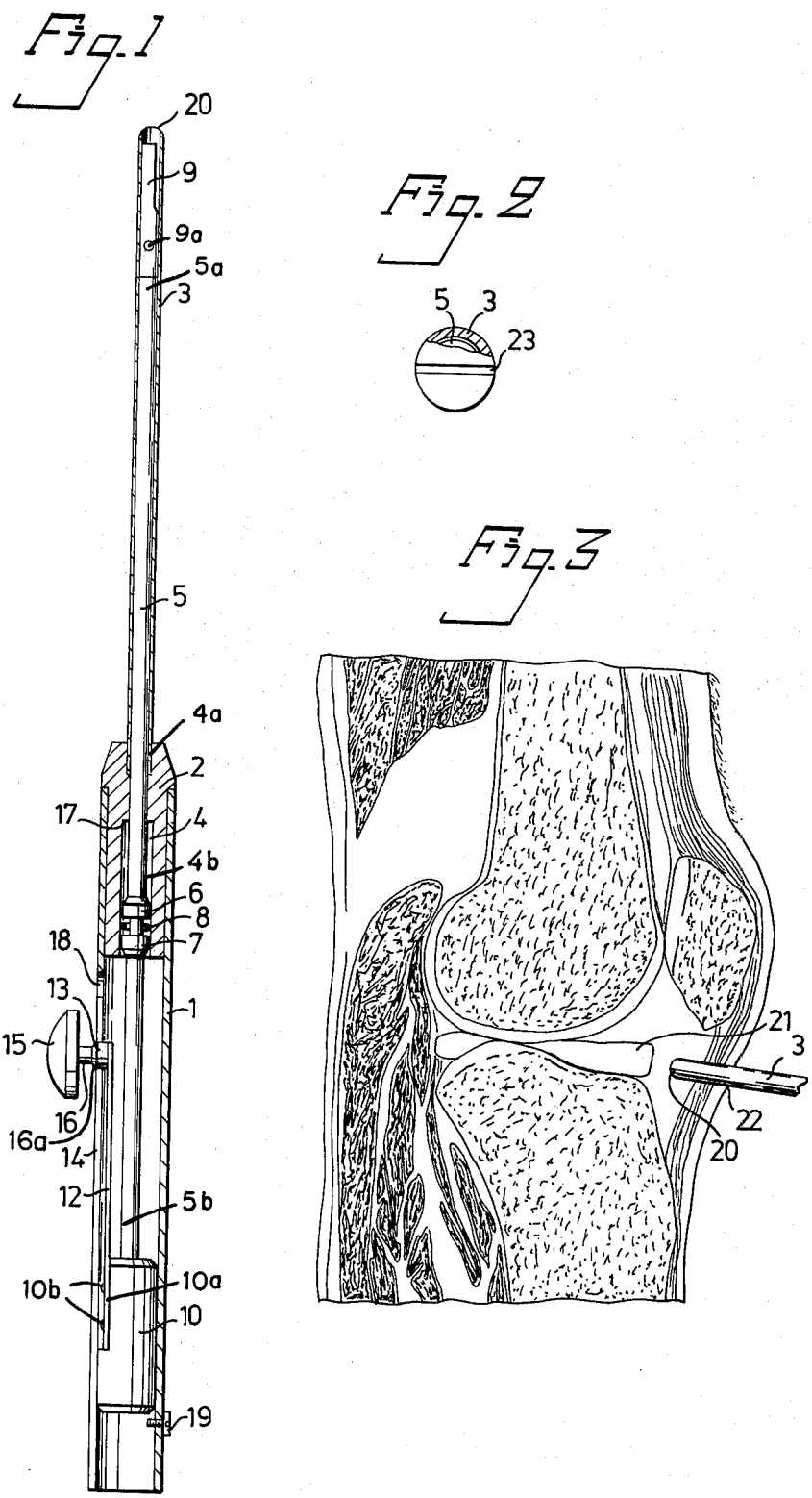

SURGICAL INSTRUMENT FOR OPERATING ON JOINTS

Injuries to body joints, such as injuries to the meniscus of a knee joint, are conventionally dealt with by opening the joint and operating on the injury by surgery, using for instance an arthroscope. After such an operation has been performed, the patient normally undergoes a period of convalescence of at least 4 to 5 weeks, whether or not the meniscus is completely or partially removed. The operation may leave a scar, which may cause difficulties later on.

Operating arthroscopes have been especially designed to avoid these disadvantages, and also reduce the time for convalescence. An operating arthroscope comprises a body portion which includes a channel for directing light into the joint; a channel for introduction of rinsing liquid; and a channel through which the operating surgical instrument can be inserted, with cutting means axially movable within the body portion. An operating arthroscope is a very clumsy and expensive instrument, and can be manipulated only in the wide interior portions of the joint. In spite of the large dimensions of the known arthroscopes the channel for the operating surgical instrument is very narrow and therefore the instrument must be very thin and, thus, fragile. Moreover, there is no way of guiding the knife as it is extended and withdrawn from the body of the instrument, or of restraining it from sideways or rotational movement, and an operating arthroscope is difficult to sterilize, because of the number of component parts, which are difficult of access.

Because the instrument is clumsy to manoeuver, it may be necessary to make a number of insertions into the joint before the instrument can be brought into a position in which the damaged meniscus can be properly operated on. Moreover, fluids in the joint may flow out through the insertion slits made and used under previous steps of the operation.

Accordingly, the present invention provides a surgical instrument especially designed for operating on joints which is independent of any light transmitting devices, which devices can accordingly be inserted independently, whereever required. This makes it possible to insert the surgical instrument in an exact position for the operation, and the design and flexibility of the instrument are such that it can be manipulated quite freely, while sealing off the joint so that body fluids cannot escape through the instrument itself.

The surgical instrument for performing operations on joints in accordance with the invention comprises, in combination, an elongated hollow body; an elongated tube fixedly connected at one end to the body, and adapted for insertion into a joint at a selected location; a manipulator shaft axially movable in the tube and in the body; a substantially planar cutting means on one end of the shaft; and means manipulatable by the fingers to move the shaft between a first position in which the cutting means is withdrawn within the tube and a second position in which the cutting means is extended beyond the end of the tube; the tube having a rounded closed end with a slot therethrough through which the cutting means is extended and withdrawn, and effective to guide the cutting means during such movement and to restrain the cutting means against rotation during such movement and while cutting.

A preferred embodiment of the invention is illustrated in the drawings in which:

FIG. 1 is a partial longitudinal section of a surgical instrument in accordance with the invention.

FIG. 2 is an end view, with parts cut away, from the insertion end of the instrument of FIG.1, showing the slot; and FIG. 3 is a sectional view through a knee joint, showing how the instrumment is inserted into the joint.

The instrument shown in FIGS. 1 to 3 has an elongated hollow body portion 1 arranged to serve as a handle, and in the form of a metal cylindrical sleeve. Press-fitted into one end of the sleeve 1 and fixed thereto is a metal insert 2, with a central bore defining a cylindrical passage 4 through the insert having enlarged portions 4a and 4b at each end and coaxial with the open interior of the cylindrical tube 3. The tube end is mounted in the enlarged portion 4a of the passage.

A cylindrical manipulator shaft 5, which can be solid, i.e. a rod, as shown but which also can be tubular, is slidably mounted within the tube 3 passage 4 and body 1, and extending the full length of the tube 3 and nearly the full length of the body 1. The shaft 5 has an exterior diameter slightly smaller than the interior diameter of the tube 3, so that an easy sliding fit is provided, but without permitting appreciable lateral displacement of the shaft 5 within the tube 3.

Within the expanded part 4b of the bore through the insert 2, the shaft 5 is provided with two spaced laterally-extending flanges 6 and 7, encircling the shaft, the outer peripheries of which closely abut the walls of the bore in a sliding fit. Between these flanges is captured an O-ring seal 8, which sealingly abuts the wall of the bore 4b, and prevents flow of fluid therepast.

At its outer end 5a, the shaft 5 carries a cutting tool or knife 9, which is substantially planar, and fixed to the shaft by the pin 9a. The knife 9 may also form an integral portion of the shaft 5. The rounded end 20 of the tube 3 is closed off, as best seen in FIG. 2, and provided with a slot 23 whose width and length corresponds to the thickness and breadth of the knife 9. The knife 9 passes through the slot 23 when the shaft 5 is moved axially outwardly or inwardly with respect to the tube 3 and the body 1.

To the opposite end 5b of the shaft is affixed a slide 10, whose external diameter is slightly less than the internal diameter of the open space within body 1, and which therefore moves slidably within the body 1 against the inner walls thereof. The slide has a cut away portion 10a, to which an axially extending leaf spring 12 is fixed by pins 10b. Attached to the free end of the leaf spring 12 is a peg 13, which extends through an elongated slot 14 in the wall of the body 1. The outer end of the peg 13 has a portion 16 of reduced diameter inserted in a recess (not shown) in a knob or button 15 which is fixed thereto in a press fit or by means of bonding or adhesive. The portion 16 joins the larger base portion of the peg 13 at tapered shoulders 16a.

The slot 14 is of a width slightly greater than the outer diameter of portion 16 of the peg, and slightly less than the outer diameter of the portion of peg 13 attached to the spring 12. Thus, when the peg is in the position shown in FIG. 1, movement of the peg 13 (and with it slide 10 and shaft 5) along the slot 14 is resisted by frictional engagement of the peg against the inner walls of the body 1 adjacent the slot 14. However, when the peg 13 is moved inwardly against the outwardly-biasing force of the leaf spring 12, so that the part 16 is within the slot, it is easy to move the button 15 and with it the leaf spring 12 and the slide 10 carrying the shaft 5 axially along the body 1 and the tube 3.

The slot 14 has a wide aperture at the end joining insert 2. the portion 18 is circular and of a diameter slightly larger than the base of peg 13. When the peg extends into aperture 18, the peg 13 and with it spring 12, slide 10 and shaft 5 are locked in position. When the button 15 and peg 13 have been pushed inwardly, the shaft 5 can be pushed along tube 3 by manipulation of the button 15. Thus, manipulation of button 15 makes it possible to move the knife 9 into or out from the tube 3 through the slot 23. When extended, it can be locked with the knife in a cutting position by putting peg 13 in aperture 18.

The extent of the outward reach of the knife 9 and shaft 5 is determined by the length of the bore 4b. When the flange 6 affixed to the shaft 5 reaches the bottom 17 of this bore, further outward movement is prevented. With the knife in this position, the button 15 and peg 13 are in aperture 18, held there by the biasing force of the spring 12. Thus, the shaft is locked with the knife 9 in the extended cutting position, in which it cannot be moved inwardly nor rotated, except upon displacement inwardly of the bottom 15, due to slot 23. While the embodiment shown in the drawing has only one notch 18, two or more notches 18 can be provided, to provide a plurality of positions for varying the protruding length of the knife 9 and shaft 5.

When the knife 9 is to be withdrawn and secured again within the tube 3, the button 15 is pressed inwardly, which releases the peg 13 from aperture 18, and permits the button to be slid along the slot 14 towards its other end, withdrawing the shaft 5 and putting the knife 9 back to the position shown in FIG. 1.

The inward limiting position of the shaft 5 is determined by the slide 10, which in that position abuts the stop screw 19. In this position, the knife 9 is completely withdrawn into the tube 3, as illustrated in the Figure.

To disassemble the instrument, and recover the knife 9 for sharpening or replacement, one simply removes the stop screw 19, after which the slide 10 and accompanying shaft 5 and knife 9 can be fully withdrawn from the body 1.

The end of the tube 3 where it is to be inserted into the body joint has a rounded and uniform end portion 20, so as not to damage soft portions of for example a joint during insertion for surgery.

The manner in which the device shown is utilized in surgery is illustrated in FIG. 3, which represents a simplified side view of a knee joint. The meniscus 21 is to be operated on at a location which has been determined by examining the meniscus directly, using an arthroscope. The arthroscope is conventional, and comprises a tubular optic device which is inserted via an obturator through an insertion made in the soft part of the knee. The insertion can be made by any known surgical device, such as a trocar, which makes a cut through the soft part. After the place where the meniscus is damaged has been located, with the aid of the arthroscope, a further incision 22 is made, and here the tube 3 of the device shown is inserted directly. The knife 9 at this stage is within the tube 3, in the position shown in FIG. 1, to prevent damage to the tissues. Since the point 20 of the tube 3 is gently rounded, the tube can be passed in and through the tissues and past the muscles without damage thereto.

After the end 20 of the tube 3 has been put in the operating position with respect to the meniscus 21, as checked by the arthroscope, the knife 9 is extended from the tube 3, and cutting begun. The instrument can be moved freely about during the entire operation, independently of any other instrument, and since a good seal is obtained between the outer surface of the tube 3 and the soft parts of the joint in the vicinity of the insertion 22, the soft parts encircling the tube 3, there is no escape of body fluids there. Neither is there any flow of body fluids through the instrument, because such flow is prevented by the O-ring seal 8. After the cutting is complete the operation is terminated by removing the cut portions of the meniscus with the aid of forceps or a similar instrument such as an obturator.

Because the muscles and tissue of the patient are not damaged to any appreciable extent by the instrument of the invention, the patient after the operation is normally able to resume work within one or two days, as compared to a normal time for convalescence of from 4 to 6 weeks, in the case of a conventional operation using conventional instruments.

Numerous modifications in the device will be apparent. For instance, the O-ring seal can be placed within the tube 3, between the shaft 5 and the tube, instead of in the insert 2. Any type of sealing means other than an O-ring seal can be used, for instance, a membrane whose edge portions are sealingly connected to the inner wall of the body, and which has a slot through which the shaft can extend.

Having regard to the foregoing disclosure, the following is claimed as the inventive and patentable embodiments thereof:

1. A surgical instrument especially designed for operating on joints which is independent of any light transmitting devices, and which can be manipulated freely while sealing off the joint so that body fluids cannot escape through the instrument itself, comprising, in combination, an elongated hollow body; an elongated cylindrical tube fixedly connected at one end to the body, and adapted for insertion into a joint at a selected location; a manipulator shaft axially movable in the tube and in the body; a substantially planar cutting means on one end of the shaft; and means manipulatable by the fingers to move the shaft between a first position in which the cutting means is withdrawn within the tube and a second position in which the cutting means is extended beyond the end of the tube; the cylindrical tube having a rounded closed end with a slot therethrough through which the cutting means is extended and withdrawn, and effective to guide the cutting means during such movement and to restrain the cutting means against rotation during such movement and while cutting.

2. A surgical instrument according to claim 1 in which the elongated hollow body portion is arranged to serve as a handle, and in the form of a metal cylindrical sleeve.

3. A surgical instrument according to claim 2 in which an insert is fixed to one end of the sleeve, the insert having a central bore defining a through cylindrical passage having enlarged portions at each end and coaxial with the open interior of the tube, and one end of the elongated tube is mounted in one enlarged portion of the passage.

4. A surgical instrument according to claim 3 in which the manipulator shaft is a rod slidably mounted within the tube, insert passage and body, and extends the full length of the tube and nearly the full length of the body, and has an exterior diameter slightly smaller than the interior diameter of the tube, so that an easy sliding fit is provided, but without permitting appreciable lateral displacement of the shaft within the tube.

5. A surgical instrument according to claim 4 wherein in the portion within an expanded part of the bore through the insert, the shaft is provided with two spaced laterally-extending flanges encircling the shaft, the outer peripheries of which closely abut the walls of the bore in a sliding fit, and between these flanges is captured a seal ring which sealingly abuts the wall of the bore and prevents flow of fluid therepast.

6. A surgical instrument according to claim 1 in which the cutting means is a knife.

7. A surgical instrument according to claim 1 in which the end of the shaft within the body is affixed to a slide whose external diameter is slightly less than the internal diameter of the open space within the body, and which moves slidably within the body against the inner walls thereof.

8. A surgical instrument according to claim 1 in which the slide has a cutaway portion to which an axially extending leaf spring is fixed.

9. A surgical instrument according to claim 8 in which a peg is attached to the free end of the leaf spring, and the wall of the body has an elongated slot through which the peg extends.

10. A surgical instrument according to claim 9 in which the outer end of the peg has a portion of reduced diameter carrying a knob for manipulative movement of the peg in the slot.

11. A surgical instrument according to claim 10 in which the slot is of a width slightly greater than the outer diameter of the portion of reduced diameter of the peg, and slightly less than the outer diameter of the portion of peg attached to the spring, so that movement of the peg and with it the slide and the shaft along the slot is resisted by frictional engagement of the peg against the inner walls of the body adjacent the slot.

12. A surgical instrument according to claim 11 in which the slot has a wide aperture at one end that is of a diameter slightly larger than the base of the peg, so that when the peg extends into the aperture the peg and with it the spring, slide and shaft are locked in position.

* * * * *